United States Patent
Murayama

(10) Patent No.: US 10,309,933 B2
(45) Date of Patent: Jun. 4, 2019

(54) PHOTOACOUSTIC MICROSCOPE

(71) Applicant: OLYMPUS CORPORATION, Tokyo (JP)

(72) Inventor: Yoshiaki Murayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 396 days.

(21) Appl. No.: 15/191,750

(22) Filed: Jun. 24, 2016

(65) Prior Publication Data

US 2016/0305912 A1    Oct. 20, 2016

Related U.S. Application Data

(63) Continuation of application No. PCT/JP2014/006182, filed on Dec. 11, 2014.

(30) Foreign Application Priority Data

Dec. 25, 2013  (JP) ................. 2013-267398

(51) Int. Cl.
*G01N 29/24*  (2006.01)
*G01N 29/44*  (2006.01)
(Continued)

(52) U.S. Cl.
CPC ....... *G01N 29/0681* (2013.01); *A61B 5/0095* (2013.01); *G01N 29/032* (2013.01);
(Continued)

(58) Field of Classification Search
CPC .......... G01N 29/2418; G01N 29/0681; G01N 29/032; G01N 29/44; G01N 29/4427;
(Continued)

(56) References Cited

U.S. PATENT DOCUMENTS 5,062,715 A * 11/1991 Nakata ............... G01N 29/2418
356/432
5,136,172 A * 8/1992 Nakata ............... G01N 21/1702
250/559.39
(Continued)

FOREIGN PATENT DOCUMENTS

CN        1401070 A      3/2003
JP     2011-519281 A     7/2011
(Continued)

OTHER PUBLICATIONS

International Search Report dated Mar. 17, 2015 issued in PCT/JP2014/006182.
(Continued)

*Primary Examiner* — Lisa M Caputo
*Assistant Examiner* — Rose M Miller
(74) *Attorney, Agent, or Firm* — Scully, Scott, Murphy & Presser, P.C.

(57) ABSTRACT

A photoacoustic microscope includes a light source, an objective lens, a light scanner, a photoacoustic wave detector, and a calculation unit. The light source emits excitation light. The objective lens focuses the excitation light within a specimen. The light scanner scans the specimen with the excitation light. The photoacoustic wave detector detects photoacoustic waves. The calculation unit uses a correlation coefficient to calculate a shift in waveform due to a change over time in photoacoustic waves between a standard position and a calculation position. The calculation unit calculates the depth from the standard position at the calculation position based on the shift.

11 Claims, 9 Drawing Sheets

(51) Int. Cl.
G01N 29/06 (2006.01)
A61B 5/00 (2006.01)
G01N 29/032 (2006.01)

(52) U.S. Cl.
CPC ......... *G01N 29/2418* (2013.01); *G01N 29/44* (2013.01); *G01N 29/4427* (2013.01); *G01N 2291/0289* (2013.01); *G01N 2291/02483* (2013.01); *G01N 2291/263* (2013.01)

(58) Field of Classification Search
CPC . G01N 2291/02483; G01N 2291/0289; G01N 21/1702; A61B 5/0095
USPC .......................................................... 73/643
See application file for complete search history.

(56) References Cited

U.S. PATENT DOCUMENTS 9,128,032 B2 * 9/2015 Carson ................ A61B 5/0059
2011/0106478 A1 * 5/2011 Someda ............... A61B 5/0059
                                                        702/104
2015/0316510 A1 * 11/2015 Fukushima .......... G02B 21/002
                                                        73/643

FOREIGN PATENT DOCUMENTS

JP      2012075511 A  *  4/2012
JP      2012-163526 A     8/2012
JP      2013-113804 A     6/2013
WO     WO-2014103106 A1 *  7/2014 ........... G02B 21/002

OTHER PUBLICATIONS

Chinese Office Action dated Mar. 13, 2018 in Chinese Patent Application No. 201480070297.7.

* cited by examiner

PHOTOACOUSTIC MICROSCOPE

CROSS-REFERENCE TO RELATED APPLICATION

The present application is a Continuing Application based on International Application PCT/JP2014/006182 filed on Dec. 11, 2014, which in turn claims priority to Japanese Patent Application No. 2013-267398 filed on Dec. 25, 2013, the entire disclosure of these earlier applications being incorporated herein by reference.

TECHNICAL FIELD

This disclosure relates to a photoacoustic microscope.

BACKGROUND

Photoacoustic waves are a kind of elastic wave that is generated during a thermoelastic process occurring when a substance is irradiated with light in a wavelength range absorbed by the substance. Photoacoustic waves have therefore attracted attention as a method for imaging absorption properties.

A photoacoustic microscope that employs photoacoustic waves as detection signals for the purpose of imaging uses, as excitation light, pulsed light corresponding to a wavelength range that is absorbed by an object under observation. The photoacoustic microscope focuses the excitation light with an objective lens to scan within a specimen using a focused spot and then detects, with a transducer or the like, a photoacoustic wave generated at each focused spot position (see JP 2011-519281 A (PTL 1)). With such a photoacoustic microscope, during the scanning of the specimen with the focused spot, a photoacoustic wave is generated when an absorbing substance is present at the focused spot position. Hence, by detecting the photoacoustic wave, the absorption properties in the specimen can be imaged.

CITATION LIST

Patent Literature

PTL 1: JP 2011-519281 A

SUMMARY

A photoacoustic microscope according to this disclosure includes:
a light source emitting excitation light;
an objective lens configured to focus the excitation light within a specimen;
a light scanner configured to change a positional relationship between the specimen and a focused position of the excitation light focused by the objective lens;
a photoacoustic wave detector configured to detect a photoacoustic wave emanating from the specimen due to irradiation with the excitation light; and
a calculation unit configured to use a correlation coefficient to calculate, relative to a change over time in a photoacoustic wave detected at a standard position that is any position within a scanning range of the specimen, a shift in waveform due to a change over time in a photoacoustic wave detected at a calculation position within the specimen other than the standard position and to calculate a depth of the calculation position from the standard position based on the shift.

DETAILED DESCRIPTION

The following describes embodiments with reference to the drawings.

Figure 1:
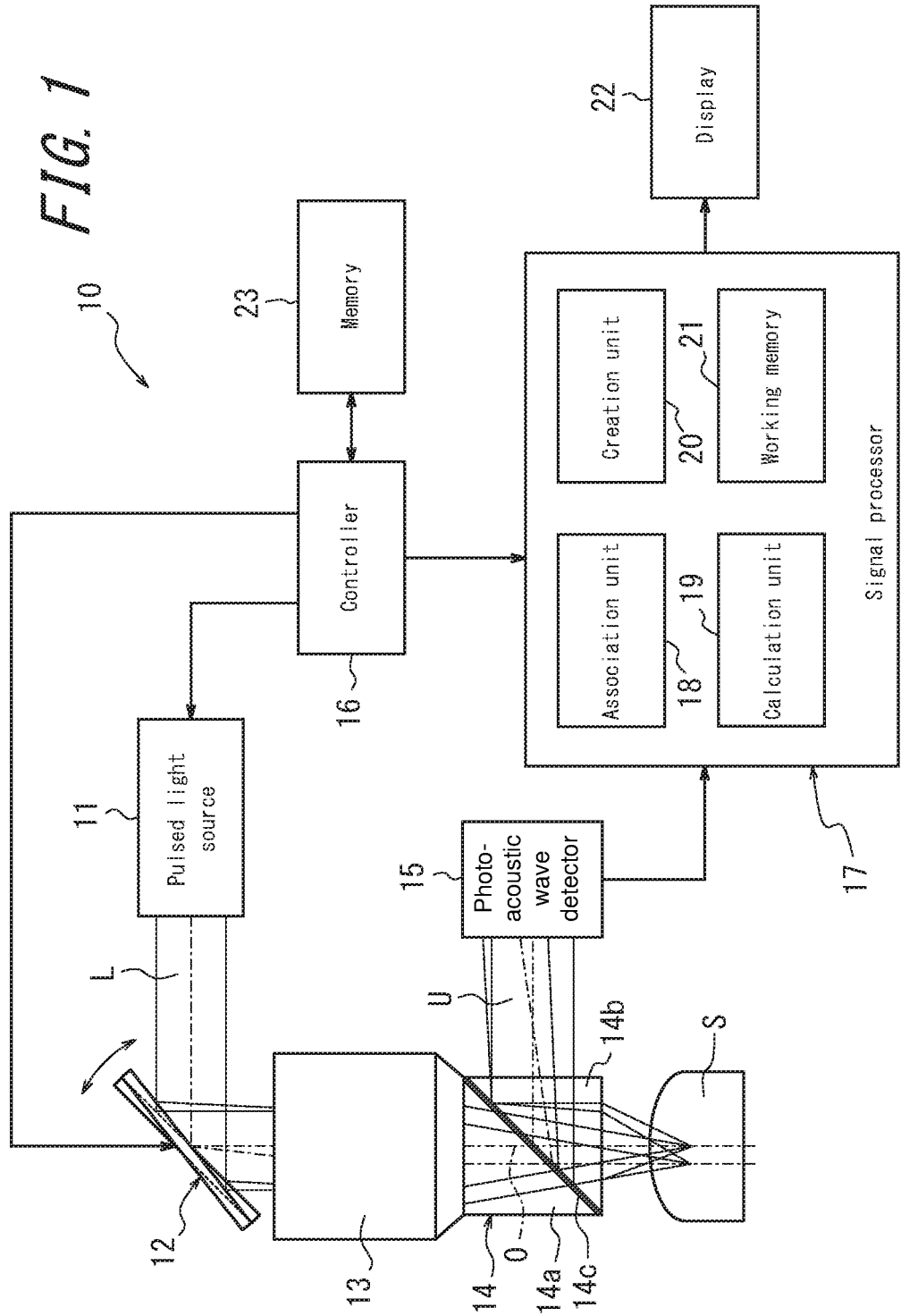
FIG. 1 schematically illustrates the main configuration of a photoacoustic microscope according to one of the disclosed embodiments.

FIG. 1 schematically illustrates the main configuration of a photoacoustic microscope according to one of the disclosed embodiments. A photoacoustic microscope 10 deflects excitation light L, emitted from a pulsed light source 11, with a light scanner 12 so that the excitation light L passes through an objective lens 13 and a photoacoustic wave reflector 14 to irradiate the inside of a specimen S as a focused spot. A photoacoustic wave U emanating from the specimen S is reflected by the photoacoustic wave reflector 14 in a different direction than the optical path of the excitation light L and is detected by a photoacoustic wave detector 15.

For example, when the specimen S is a living organism and blood vessels within the organism are to be imaged, the pulsed light source 11 emits excitation light L with the absorption wavelength of hemoglobin. The target of observation is not, however, limited to blood vessels. This disclosure may also be applied to imaging of endogenous substances such as melanin. In this case, light in the absorption wavelength region of the substance to be observed is used as the excitation light L. This disclosure may also be applied to imaging of exogenous substances such as fluorescent material, metal nanoparticles, or the like. In this case, light in the absorption wavelength region of the targeted fluorescent material or light in the resonant wavelength region of the targeted metallic nanoparticles is used as the excitation light L. When a plurality of absorbing substances are present within the specimen S, it is preferable to use light at the peak wavelength of the characteristic absorption spectrum of the object under observation. In the pulsed light source 11, the emission timing of the pulsed light is controlled by a controller 16.

The light scanner 12 for example includes two galvanometer mirrors, the driving of which is controlled by the controller 16 in synchronization with the emission timing of the pulsed light source 11, so that the inside of the specimen S is two-dimensionally scanned by the focused spot of the excitation light L. Since it suffices for the light scanner 12 to be able to change the relative positional relationship between the focused spot of excitation light L and the specimen, the light scanner 12 may be configured instead to change the position of the specimen or the position of a stage or the like on which the specimen is placed.

As the objective lens 13, lenses with different focal lengths are appropriately selected and mounted.

The photoacoustic wave reflector 14 includes two right triangular prisms 14a and 14b, the inclined faces of which are joined by a photoacoustic wave reflection member 14c. The photoacoustic wave reflection member 14c is transparent with respect to the excitation light L and is formed from a member with a different acoustic impedance than the right triangular prism 14b at the specimen S side, such as silicone oil or air. Since the difference between the acoustic impedance of the right triangular prism 14b and the acoustic impedance of the photoacoustic wave reflection member 14c satisfies a predetermined relationship, the photoacoustic wave U is reflected by the photoacoustic wave reflection member 14c. A non-illustrated acoustic wave lens may be disposed at the specimen S side of the right triangular prism 14b.

The excitation light L passing through the objective lens 13 and the photoacoustic wave reflector 14 is focused on the focusing position of the objective lens 13. The specimen S is disposed so as to overlap with the focused spot of the excitation light L. The photoacoustic wave U emanating from the focused spot position of the excitation light L in the specimen S is incident on the right triangular prism 14b. At the interface between the right triangular prism 14b and the photoacoustic wave reflection member 14c, the photoacoustic wave U is reflected in a different direction than the optical path of the excitation light L and exits from the right triangular prism 14b into the photoacoustic wave detector 15. The space between at least the objective lens 13 and the specimen S and between the right triangular prism 14b and the photoacoustic wave detector 15 is preferably filled with a photoacoustic wave transmission medium, such as water, through which the photoacoustic wave U easily propagates.

The photoacoustic wave detector 15 may, for example, be a transducer that detects the photoacoustic wave U exiting from the right triangular prism 14b. The photoacoustic wave detector 15 outputs the waveform of the change in intensity of the photoacoustic wave U relative to the change over time to a signal processor 17 as an output signal.

The signal processor 17 includes an association unit 18, a calculation unit 19, a creation unit 20, and a working memory 21.

Figure 2:
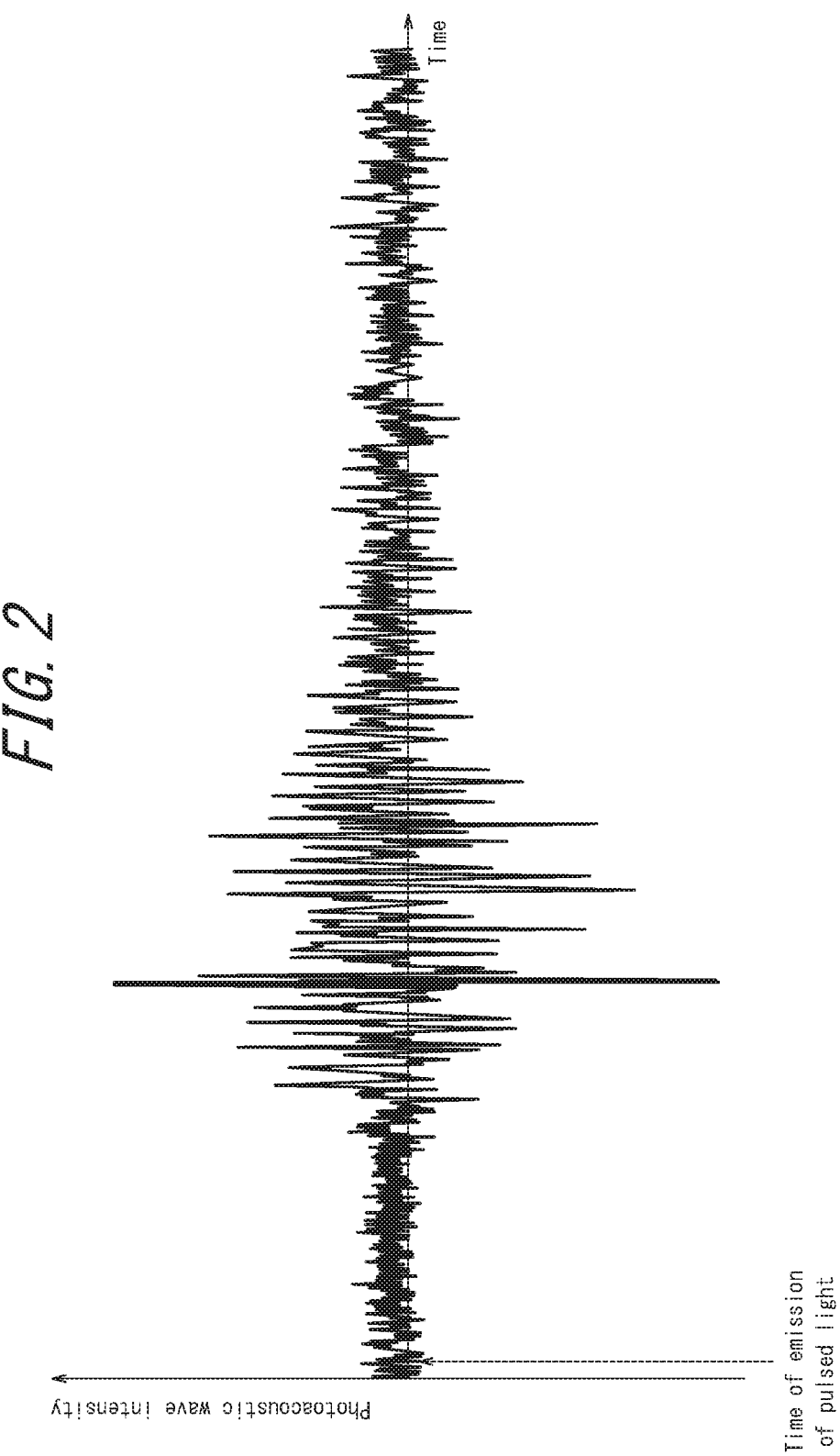
FIG. 2 is a graph illustrating the change over time in the intensity of the acoustic wave detected by the acoustic wave detector in FIG. 1.

In synchronization with the driving of the light scanner 12 by the controller 16, i.e. in synchronization with the irradiation timing of the excitation light L when two-dimensionally scanning the specimen S in a plane orthogonal to the optical axis O of the objective lens 13, the association unit 18 associates, based on an output signal obtained from the photoacoustic wave detector 15, the irradiation position of the excitation light L and the output signal. The association unit 18 may also associate the beginning of the output signal, i.e. the beginning of the change in intensity of the photoacoustic wave U relative to the change over time (see FIG. 2), with the time of emission of the pulsed light at the irradiation position.

As described below, the calculation unit 19 calculates the correlation coefficient between the output signal at the standard position and at a calculation position other than the standard position, and based on this correlation coefficient, calculates the depth at the calculation position.

Figure 3:
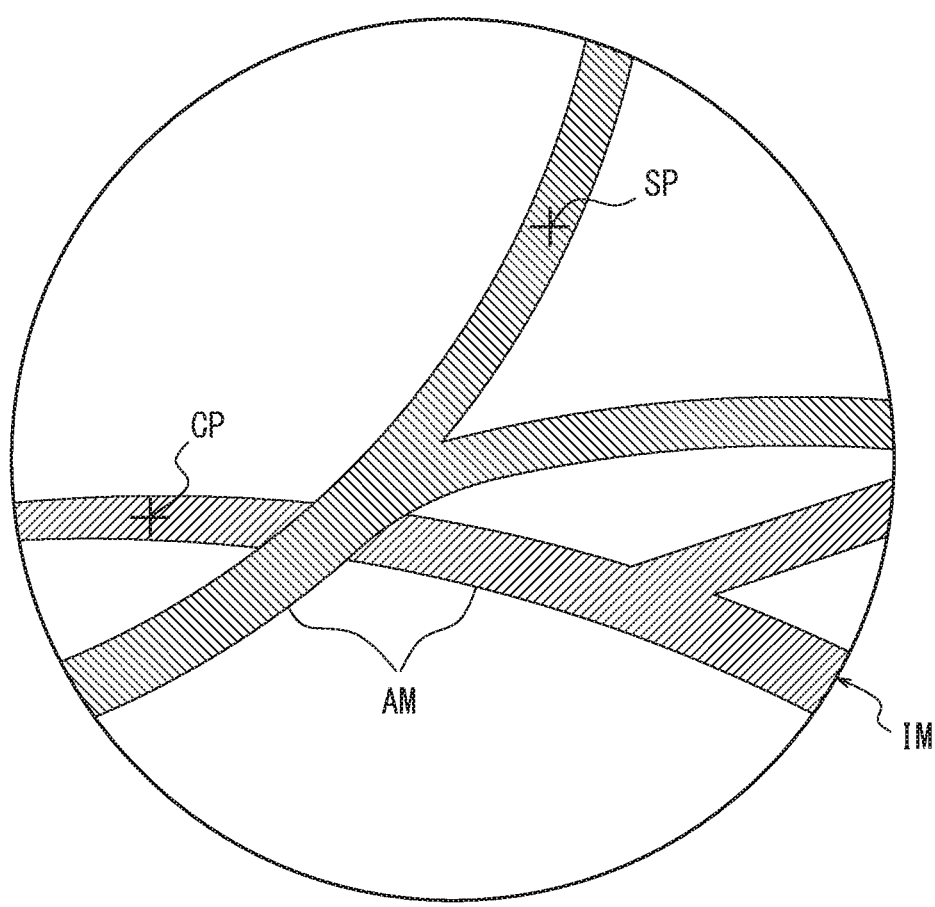
FIG. 3 illustrates an example of an image corresponding to the intensity distribution of the acoustic waves generated by a specimen.

The standard position is a position at which a substance similar to the substance at the calculation position is present and may be set to a position irradiated by light with approximately the same intensity as the light irradiating the calculation position. In greater detail, the standard position may be set to any position among all of the irradiation positions of the excitation light L. As described below, the standard position may be set by an observer who uses a pointing device, such as a mouse, to designate any position on an image that is created by the creation unit 20 and displayed on a display 22. By automatically analyzing the output signal obtained from the photoacoustic wave detector 15, the standard position may be set to a position exhibiting high intensity. The calculation of depth can be made for an absorbing substance that generates a photoacoustic wave U. Therefore, as illustrated in FIG. 3, the observer can designate any point in an image of an absorbing substance within an image IM created by the creation unit 20 to be a standard position SP (see FIG. 3).

Figure 4:
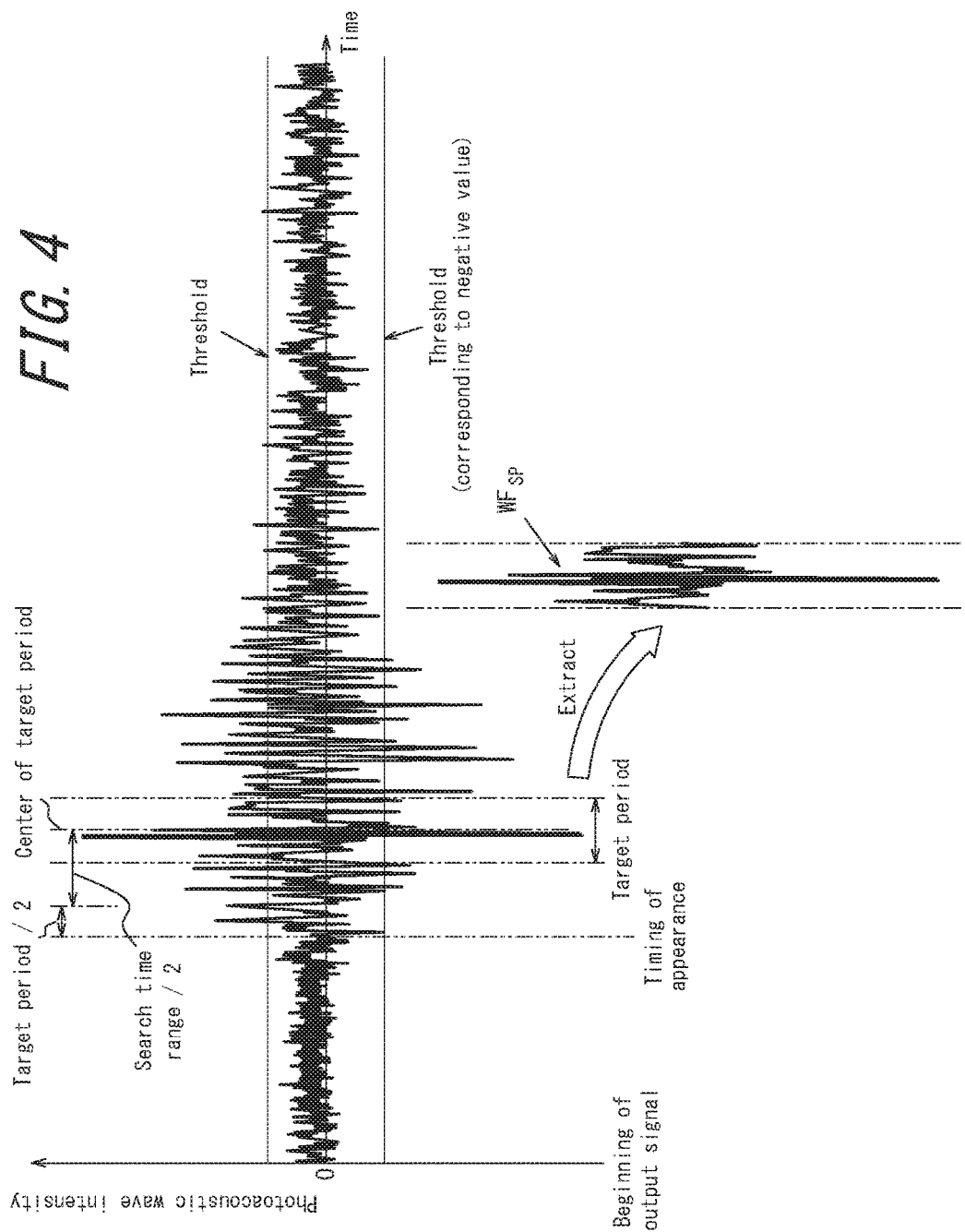
FIG. 4 is a graph illustrating the waveform of an output signal associated with a standard position.

Within the output signal associated with the standard position SP, the calculation unit 19 detects the timing of the appearance of the photoacoustic wave U. As illustrated in FIG. 4, the timing of the appearance refers to the timing at which, in the waveform corresponding to the output signal, the absolute value of the intensity of the photoacoustic wave U exceeds a threshold. The threshold may be set to any value that can exclude white noise occurring in the state when the photoacoustic wave U does not appear. For example, the threshold may be set to three times the root mean square of the amplitude of white noise that is typically sampled.

Based on the detected timing of the appearance, the calculation unit 19 determines the time position of the target period at the standard position SP. The target period refers to the period of time over which a portion of the waveform corresponding to the output signal is extracted in order to calculate the correlation coefficient. When determining the depth of the objective lens 13, the target period is determined in advance to be equal to or greater than this depth divided by the acoustic velocity. The depth is taken to be the depth, during Berek type photography, $\pm\lambda/NA^2$ (where $\lambda$ is the wavelength of the excitation light L and NA is the numerical aperture of the objective lens 13). The time position is a coordinate along the time coordinate axis and indicates a particular time. The time position of the target period is set so that the center of the target period matches an elapsed time, from the timing of the appearance, equal to half of the total of the target period and the search time range. The search time range is described below. The calculation unit 19 extracts the waveform of the target period at the standard position SP (see the label "$WF_{SP}$" in FIG. 4). The target period may be stored in a memory 23 in association with the objective lens 13.

Figure 5:
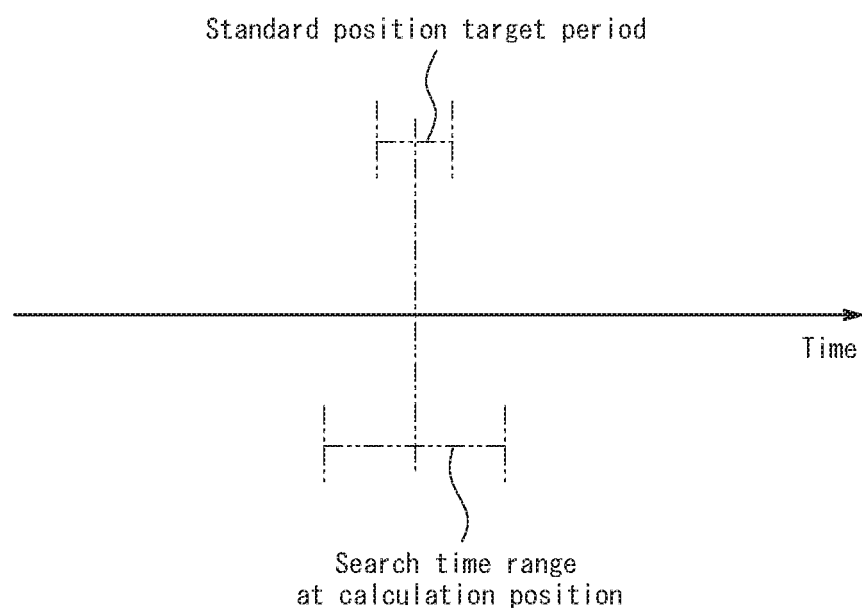
FIG. 5 illustrates the time position of the search time range with respect to the time position of the target period at the standard position.

The calculation unit 19 determines the time position of the search time range. The search time range is now described. As described below, the calculation unit 19 compares the waveform $WF_{SP}$ extracted at the standard position SP with the waveform at the calculation position CP (see FIG. 3). For comparison, waveforms within the target period at a variety of time positions are also extracted from the output signal associated with the calculation position CP. The search time range indicates the range, within the output signal at the calculation position CP, of time positions at which waveforms used to calculate the correlation coefficient are extracted. The length of the search time range may be set to any value that is less than the emission cycle of the pulsed excitation light L. For example, the length may be set in advance to twice the result of dividing the aforementioned depth of the objective lens 13 by the acoustic velocity. The time position of the search time range may be set to a time such that the center of the search time range matches the center of the target period at the standard position SP (see FIG. 5). The length of the search time range may be stored in the memory 23.

Figure 6:
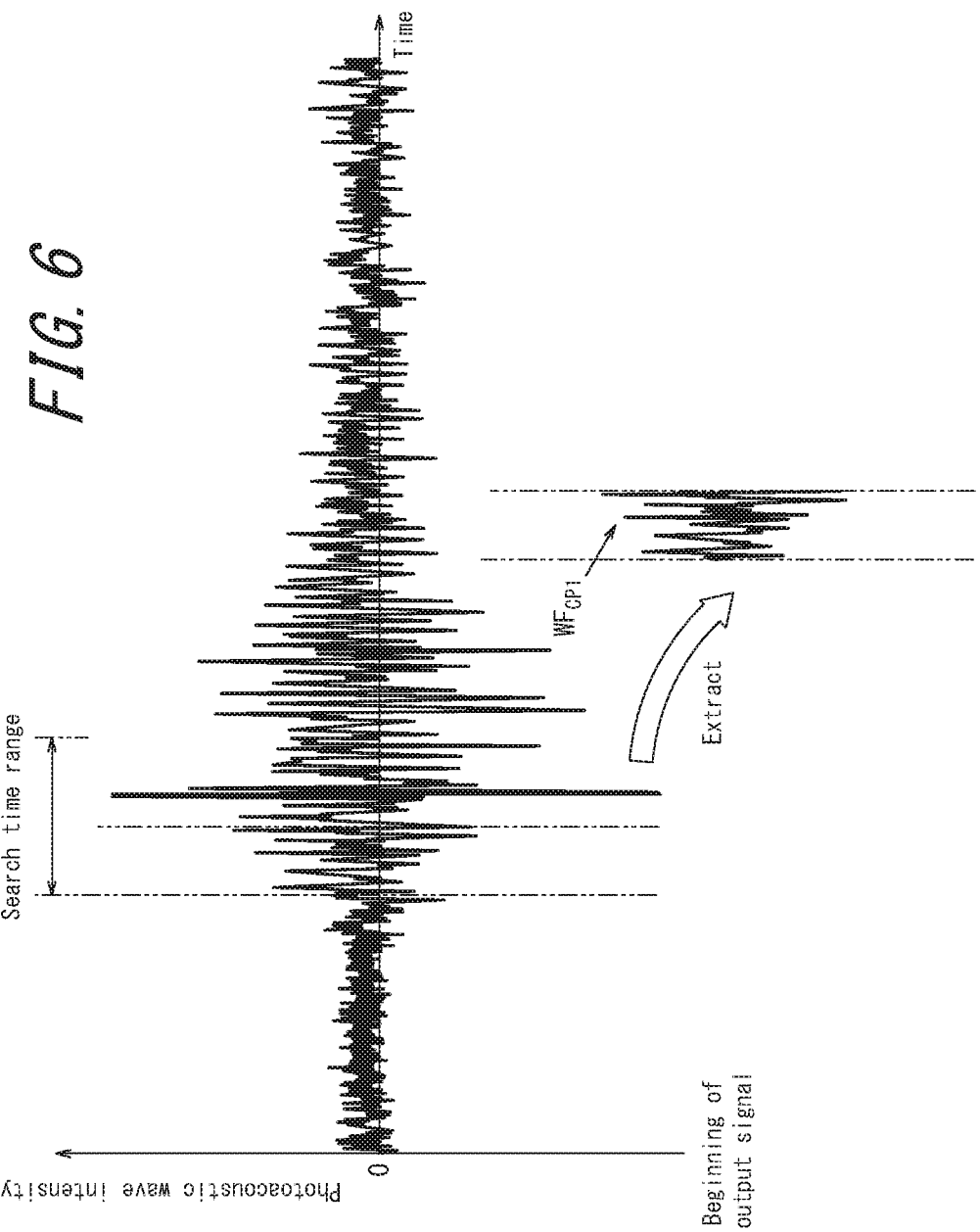
FIG. 6 is a graph illustrating the waveform of an output signal associated with a calculation position.

At the calculation position CP, the calculation unit 19 first extracts a waveform $WF_{CP1}$. The beginning of the target period of the waveform $WF_{CP1}$ matches the beginning of the search time range (see FIG. 6). The length of the waveform $WF_{CP1}$ is preferably equivalent to the length of the waveform $WF_{SP}$. The calculation unit 19 calculates the correlation coefficient between the extracted waveforms $WF_{SP}$ and $WF_{CP1}$ in the target period at the standard position SP and the calculation position CP. The calculation unit 19 stores the calculated correlation coefficient in the working memory 21.

Figure 7:
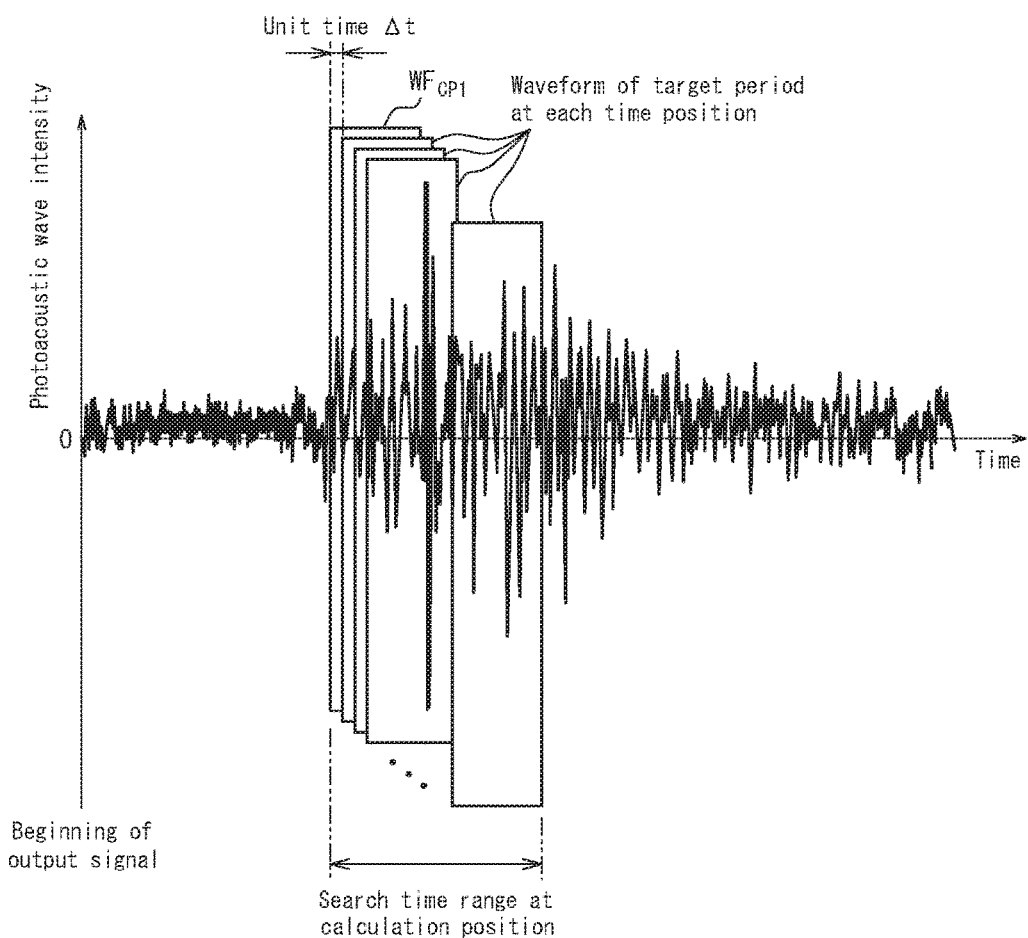
FIG. 7 illustrates the relationship between a plurality of time positions in the target period of the waveform extracted at the calculation position.

Next, the calculation unit 19 extracts a waveform in the target period at the calculation position CP by shifting the time position of the target period backward by a unit time $\Delta t$ (see FIG. 7). The unit time $\Delta t$ may be set in advance to any interval, such as the minimal time interval of the digitized output signal. The calculation unit 19 calculates the correlation coefficient between the waveform at the standard position SP and the newly extracted waveform of the target period at the calculation position CP. The calculation unit 19 stores the calculated correlation coefficient in the working memory 21. The unit time $\Delta t$ may be stored in the memory 23.

Subsequently, while shifting the time position of the target period at the calculation position CP until the end of the target period matches the end of the search time range, the calculation unit 19 repeatedly extracts the waveform of the target period at the calculation position CP, calculates the correlation coefficient between the newly extracted waveform and the waveform at the standard position SP, and saves the correlation coefficient.

Figure 8:
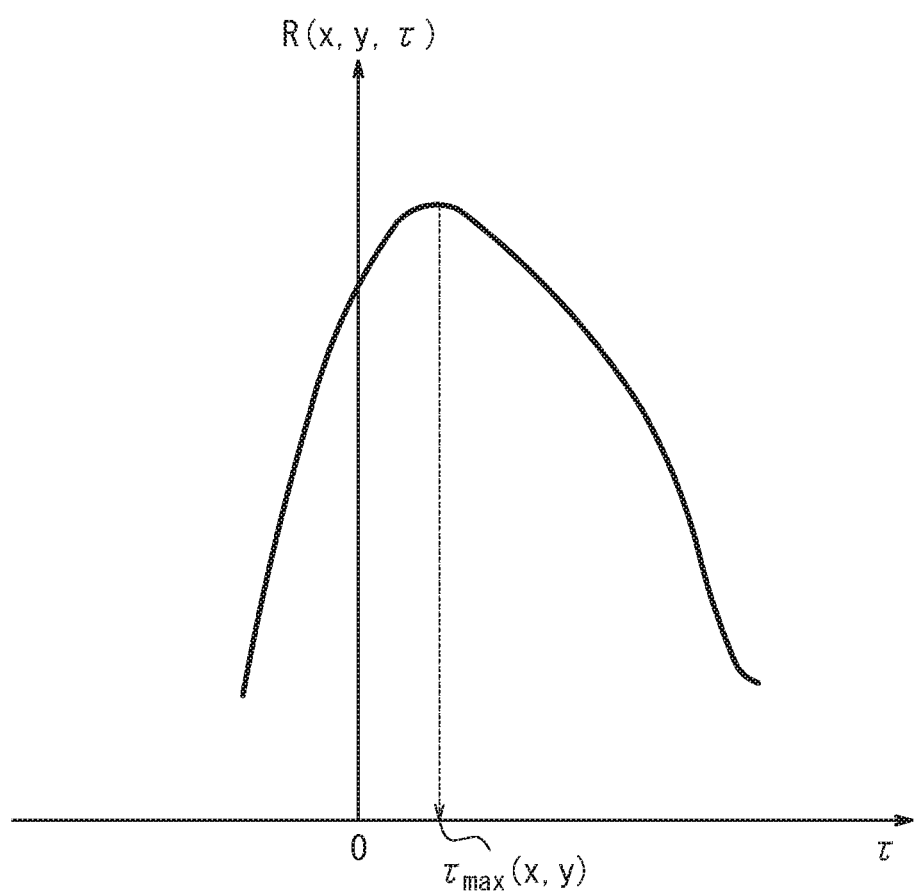
FIG. 8 is a graph illustrating the change in the correlation coefficient with respect to the lag time.

The calculation unit 19 reads the correlation coefficient, stored in the working memory 21, at each of a plurality of time positions in the search time range. The correlation coefficient is a function represented by Equation (1), and a curve is typically drawn, as illustrated in FIG. 8.

$$R(x, y, \tau) = \frac{\sum_{t=t1}^{t2}[a(x_b, y_b, t) - a_{ave,b}] \times [a(x, y, t-\tau) - a_{ave}]}{\sqrt{\sum_{t=t1}^{t2}[a(x_b, y_b, t) - a_{ave,b}]^2} \times \sqrt{\sum_{t=t1}^{t2}[a(x, y, t-\tau) - a_{ave}]^2}} \quad (1)$$

In Equation (1), $R(x, y, \tau)$ is the correlation coefficient between the waveform of the target period, where the time position is $\tau$, at the calculation position CP (coordinates $(x, y)$) and the waveform of the target period at the standard position SP (coordinates $(x_b, y_b)$). Furthermore, $a(x_b, y_b, t)$ is the amplitude at the standard position SP (coordinates $(x_b, y_b)$) at time t. The term $a(x, y, t-\tau)$ represents the amplitude at the calculation position CP when the target period is a time position shifted by the time $\tau$ relative to the time position of the target period of the standard position SP. The term t1 represents the beginning of the target period at the standard position SP, and the term t2 represents the end of the target period at the standard position SP. The term $a_{ave,b}$ represents the average amplitude at the standard position SP. The term $a_{ave}$ represents the average amplitude at the calculation position CP.

The calculation unit 19 calculates the difference between the time position of the target period at the calculation position CP and the time position of the target period of the standard position SP for the maximum correlation coefficient among the read correlation coefficients and sets the difference to be the lag time $\tau_{max}(x, y)$. By multiplying the detected lag time $\tau_{max}(x, y)$ by the acoustic velocity, the calculation unit 19 calculates the relative depth of the calculation position CP relative to the standard position SP at the calculation position CP. At other calculation positions CP, the calculation unit 19 similarly calculates the relative depth relative to the standard position SP.

The calculation unit 19 detects the time position for which the absolute value of the amplitude of the output signal associated with the standard position SP is maximized. The calculation unit 19 calculates the depth of the absorbing substance at the standard position SP based on this time position, the time of emission of the pulsed light, and the distance from the photoacoustic wave detector 15 to the specimen surface. The distance from the photoacoustic wave detector 15 to the specimen surface may be calculated based on the time from when a signal is emitted from the photoacoustic wave detector 15 towards the specimen surface until light returning from the specimen surface reaches the photoacoustic wave detector 15.

The calculation unit 19 calculates the depth of each calculation position CP by adding the depth of the standard position SP to the relative depth of each calculation position CP. The calculation unit 19 stores the calculated depth in association with each calculation position CP in the working memory 21.

In the output signal associated with each irradiation position of the excitation light L, the creation unit 20 detects the maximum of the absolute value of the amplitude and the time position at which the maximum is detected by the photoacoustic wave detector 15. The creation unit 20 calculates a value corresponding to the maximum of the absolute value of the amplitude at each irradiation position as a luminance value at each irradiation position. In other words, the creation unit 20 creates an image IM (see FIG. 3) corresponding to the detected photoacoustic waves U and the irradiation positions specified by a relative amount of change with respect to the specimen at the focused position of excitation light L, i.e. an image IM corresponding to the intensity distribution of the photoacoustic waves U of the specimen S based on the output signals. As described above, in order to designate the standard position SP, the creation unit 20 transmits the uncorrected image IM, described below, to the display 22 for display.

The creation unit 20, however, calculates the luminance value only for irradiation positions such that the time position, at which the maximum is detected by the photoacoustic wave detector 15, is in a time range corresponding to a depth that is twice the depth of $\lambda/NA^2$, centering on the focusing position of the objective lens 13. In other words, the creation unit 20 only images an absorbing substance existing in a range that is twice the focal depth of the objective lens 13.

Figure 9:
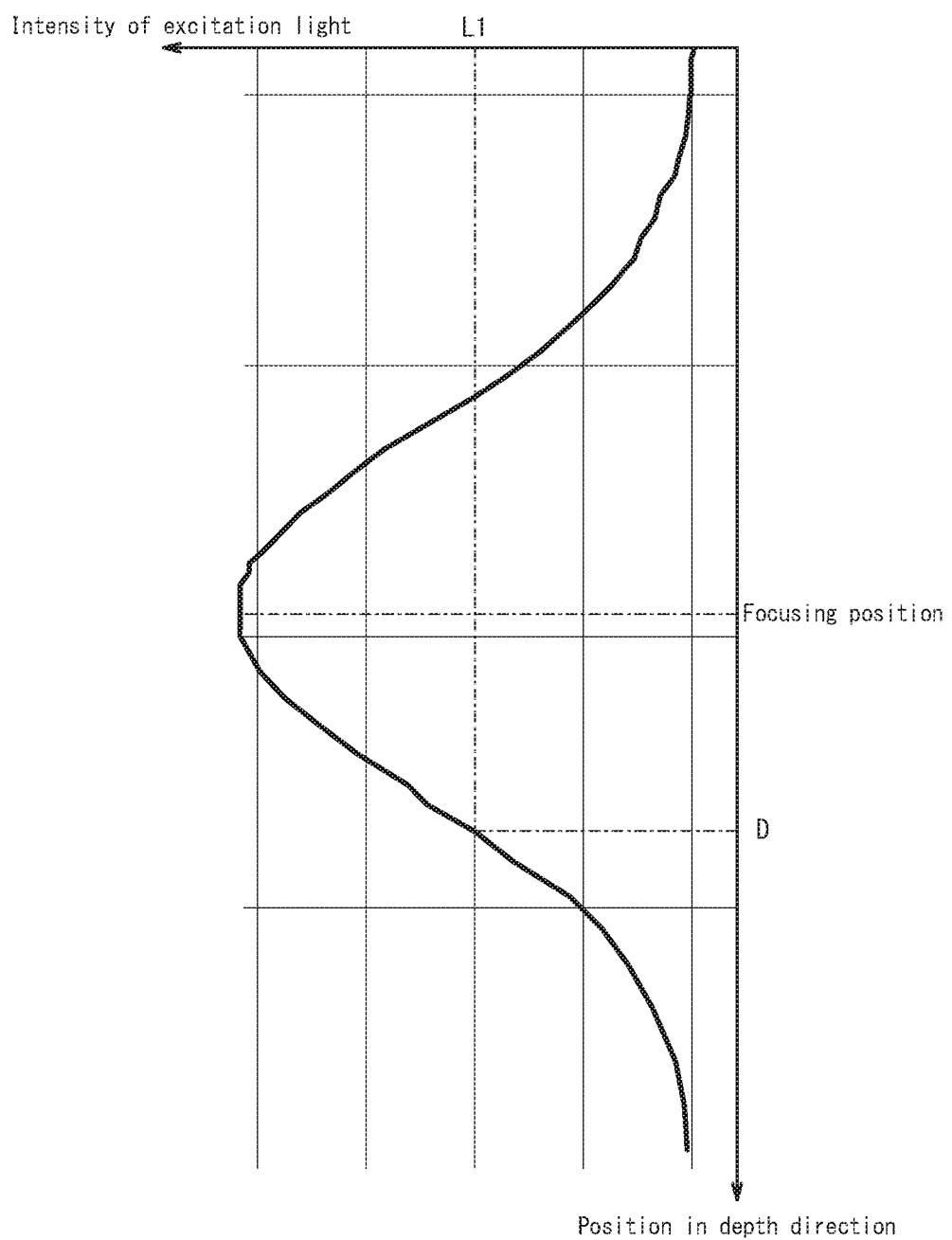
FIG. 9 is a graph illustrating the intensity of light with respect to a position in the depth direction near the position corresponding to the focal length of the excitation light.

Based on the depth of the standard position SP and the calculation position CP as calculated by the calculation unit 19, the creation unit 20 corrects the luminance of the image IM corresponding to the intensity distribution of the photoacoustic waves U. The amplitude of the photoacoustic wave U varies depending on the intensity of light with which the absorbing substance is irradiated. As illustrated in FIG. 9, the intensity of light reaches a maximum at the focusing position of the objective lens 13 and reduces in accordance with distance from the focusing position. Accordingly, the intensity of the photoacoustic wave U of any absorbing substance reduces in accordance with distance from the focusing position. Therefore, for absorbing substances present at any depth, the creation unit 20 performs correction so that the image IM is based on the photoacoustic wave U when light with the same intensity is irradiated.

The intensity of light relative to the distance from the focusing position can be calculated with a Point Spread Function (PSF) unique to a combination of the excitation light L and the specimen S. For correction, the creation unit 20 reads, from a PSF stored in advance, the intensity of light (label "LI") corresponding to the difference in the depth direction between (i) the depth of the standard position SP and each calculation position CP (see label "D") and (ii) the focusing position. The creation unit 20 calculates a correction coefficient by dividing the intensity of light at the focusing position by the read intensity of light. The creation unit 20 then performs correction by multiplying the luminance value at the standard position SP and at each calculation position CP by the correction coefficient.

Correction may also be performed to convert the luminance values of all of the absorbing substances in any specimen S to particular values. The absorbing substance that is under observation by the photoacoustic microscope 10 may be a single type of absorbing substance in any specimen S, such as a capillary underneath the surface of the specimen S. Therefore, it can be assumed that a photoacoustic wave U with the same intensity will be generated for light of the same intensity.

The creation unit 20 adjusts the luminance value as described above only for absorbing substances present within a range that is a depth of $\lambda/NA^2$ from the focusing position of the objective lens 13, in particular within a range that is twice this depth to take aberration into account. The creation unit 20 outputs the image IM with corrected luminance values to the display 22 for display.

The controller 16 controls overall operations by the photoacoustic microscope 10. The memory 23 is connected to the controller 16. An operation program and the like for the controller 16 are stored in the memory 23 as necessary. The memory 23 may be internal memory of the controller 16.

The photoacoustic microscope according to the above-described embodiment can, based on the correlation coefficient, calculate the lag in the time of arrival at the photoacoustic wave detector 15 of the photoacoustic wave U at the calculation position CP relative to the photoacoustic wave U at the standard position SP to a high degree of accuracy. The accurate lag in time of arrival and the depth of the absorbing substance are correlated. Therefore, in this embodiment, the relative depth of the absorbing substance can be calculated to a high degree of accuracy based on the lag in the time of arrival.

The photoacoustic microscope of this embodiment corrects the image IM based on the depth of the absorbing substance. Therefore, misidentification of the same type of absorbing substance as a different type of absorbing substance based on a difference in luminance due to a difference in depth can be prevented.

The photoacoustic microscope of this embodiment corrects the depth-based image IM based on a PSF and can therefore image the photoacoustic wave U in a state of radiation by light with the same intensity, regardless of depth. Accordingly, the observer can better grasp the state of the specimen S.

The photoacoustic microscope of this embodiment also performs correction to set the luminance to a constant value, regardless of depth. Therefore, misidentification of the same type of absorbing substance as a different type of absorbing substance can be prevented. Furthermore, since adjustment is preformed regardless of depth, high-load image processing is unnecessary.

The photoacoustic microscope of this embodiment images absorbing substances present in a range that is twice the depth of the objective lens 13, thus allowing visual confirmation of absorbing substances present in a range near the position corresponding to the focal length. Absorbing substances outside of this range can be imaged by adjusting the focusing position of the objective lens 13.

The photoacoustic microscope of this embodiment adjusts the luminance of the image IM of the absorbing substances present in the depth range of the objective lens 13. Therefore, absorbing substances that are close in the depth direction can be displayed with the same luminance. Accordingly, the observer can visually distinguish between a group of absorbing substances that are relatively close to the position corresponding to the focal length and a group of absorbing substances that are relatively far from the focusing position.

The photoacoustic microscope of this embodiment can calculate a correlation coefficient that highly reflects the resemblance between waveforms, since the target period is set to a value that is greater than or equal to the depth of the objective lens 13 divided by the acoustic velocity. As a result, the relative depth can be calculated to a high degree of accuracy.

With the photoacoustic microscope of this embodiment, the center position of the target period at the standard position SP is set to an elapsed time, from the timing of the appearance of the photoacoustic wave U, equal to half of the total of the target period and the search time range. Therefore, the target period at the calculation position CP can be set to be at or later than the timing of the appearance of the photoacoustic wave U at the standard position SP. Accordingly, an unnecessary processing load to calculate the correlation coefficient before the appearance of the photoacoustic wave U can be prevented.

It is to be noted that various changes and modifications will be apparent to those skilled in the art based on the drawings and embodiments described in this disclosure. Therefore, such changes and modifications are to be understood as included within the scope of the disclosure.

The invention claimed is:

1. A photoacoustic microscope comprising:
    a light source configured to emit excitation light;
    an objective lens configured to focus the excitation light within a specimen;
    a light scanner configured to change a positional relationship between the specimen and a focused position of the excitation light focused by the objective lens;
    a photoacoustic wave detector configured to detect photoacoustic waves emanating from the specimen due to irradiation with the excitation light; and
    a processor comprising hardware, wherein the processor is configured to:
        receive a standard position waveform of change in intensity of a first photoacoustic wave over time detected at a standard position within a scanning range of the specimen;

receive a calculation position waveform of a change in intensity of a second photoacoustic wave over time detected at a calculation position within the scanning range of the specimen other than the standard position;

calculate a correlation coefficient between the standard waveform and the calculation waveform;

calculate a shift in the calculation position waveform relative to the standard position waveform based on the correlation coefficient; and calculate a depth of the calculation position from the standard position based on the shift.

2. The photoacoustic microscope of claim 1,
wherein the processor is configured to create an image corresponding to intensity distribution of the photoacoustic waves emanating from the specimen based on at least the standard position waveform and the calculation position waveform.

3. The photoacoustic microscope of claim 2,
wherein the processor is configured to correct the image based on the depth.

4. The photoacoustic microscope of claim 3,
wherein the processor is configured to correct the image based on a point spread function at a position displaced based on the depth, along an optical axis, from the focused position of the objective lens.

5. The photoacoustic microscope of claim 2,
wherein the processor is configured to convert an intensity of the standard position waveform and an intensity of the calculation position waveform to a constant value.

6. The photoacoustic microscope of claim 2,
wherein the processor is configured to create, based on the depth, the image in a range within twice a focal depth of the objective lens.

7. The photoacoustic microscope of claim 3,
wherein the processor is configured to correct, based on the depth, the image for an absorbing substance present in a range within twice a focal depth of the objective lens.

8. The photoacoustic microscope of claim 1,
wherein the processor is configured to calculate the correlation coefficient in a range within twice a focal depth of the objective lens.

9. The photoacoustic microscope of claim 1,
wherein the processor is configured to:
calculate a plurality of possible correlation coefficients, wherein each of the plurality of possible correlation coefficients is between:
a portion of the standard position waveform in a target period with a set time position; and
each of a plurality of portions of the calculation position waveform in the target period, wherein a time position of the target period of the each of the plurality of portions of the calculation position waveform is displaced from one another within a predetermined search time range; and
select a maximum one of the plurality of possible correlation coefficients as the correlation coefficient.

10. The photoacoustic microscope of claim 9,
wherein the target period is greater than or equal to a focal depth of the objective lens divided by an acoustic velocity.

11. The photoacoustic microscope of claim 9,
wherein a time position of a center of the target period at the standard position is an elapsed time, from a timing of appearance of the first photoacoustic wave, equal to half of a total of the target period and the search time range.

* * * * *